United States Patent [19]

Rosen

[11] Patent Number: 5,033,304
[45] Date of Patent: Jul. 23, 1991

[54] METHOD AND APPARATUS FOR LASER ULTRASONIC CHARACTERIZATION OF COATED FIBERS

[75] Inventor: Moshe Rosen, Rockville, Md.

[73] Assignee: Industrial Quality, Inc., Gaithersburg, Md.

[21] Appl. No.: 344,222

[22] Filed: Apr. 27, 1989

[51] Int. Cl.$^5$ .............................................. G01N 29/00
[52] U.S. Cl. ......................................... 73/597; 73/602
[58] Field of Search ................. 73/597, 599, 602, 653, 73/655, 601

[56] References Cited

U.S. PATENT DOCUMENTS

| 4,346,599 | 8/1982 | McLaughlin et al. | 73/597 |
| 4,481,820 | 11/1984 | Thomann | 73/597 |
| 4,493,217 | 1/1985 | Engler et al. | 73/861.27 |
| 4,622,853 | 11/1986 | Leugers | 73/597 |
| 4,674,332 | 6/1987 | Pace et al. | 73/597 |
| 4,710,030 | 12/1987 | Tauc et al. | 356/432 |
| 4,754,645 | 7/1988 | Piche et al. | 73/597 |

OTHER PUBLICATIONS

"Laser Ultrasonics Measurement of Elastic Constants of Composites", by L. Piché et al. Material Evaluation No. 45, Feb. 1987.
E. Bourkoff and C. H. Palmer, "Noncontact Material Using Low-Energy Optical Generation and Detection of Acoustic Pulses", Review of Progress in *Quantitative Nondestructive Evaluation*, vol. 5A, 1986, p. 659.
D. A. Hutchins and J. H. Page, "Phase Insensitive Detection of Laser-Generated Ultrasound", *Applied Physics Letter*, 48, Feb. 3, 1986, p. 323.
M. Rosen, et al., "Ultrasonic Nondestructive Materials Characterization of Rapidly Solidified Microstructures", The *John Hopkins University Center for Materials Research Annual Report*, Aug. 1983, p. 45.
M. J. Rudd, "Ultrasonic Nondestructive Evaluation Using Laser Transducers" *Review of Progress in Quantitive Nondestructive Evaluation*, vol. 2B, 1983, p. 1763.
J. I. Burov et al., "High Accuracy Noncontact Laser-Optical Method for Measuring Surface Accoustic Wave Velocity and Attenuation", Applied Physics Letter, 46, Jan. 15, 1985, p. 141.
L. Piché et al., "Laser Ultrasonics Measurement of Elastic Constants of Composites", Materials Evaluation, vol. 74, Jan.-Feb. 1987, p. 74.
R. Eby et al., "Characterization of Carbon Fibers", CNDE, Naval Surface Weapons Center, Air Force Office of Scientific Research Apr. 27, 1988.
M. Rosen, "Ultrasonic Nondestructive Characterization of Metallurgical Reactions", *Traitement du Signal*, vol. 2, p. 243 (1985).
M. Rosen et al., "Ultrasonic Nondestructive Characterization (NDC) of Metallurgical Microstructures and Transformations", *The John Hopkins University Center for Materials Research Annual Report*, Sep. 1982, p. 31.
R. White, "Generation of Elastic Waves by Transient Surface Heating", J. Appl. Phys., vol. 34, No. 12, pp. 3559-3567 (Dec. 1963).
J. Ready, "Effects Due to Absorption of Laser Radiation", J. Appl. Phys., vol. 36, No. 2, pp. 462-483 (Feb. 1965).
D. Hutchins et al., "Surface Waves Using Laser Generation and Electromagnetic Acoustic Transducer Detection", IEEE Trans. Ultrasonics, Ferroelectrics, and Freq. Control, vol. UFFC-33, No. 5, pp. 478-483 (Sep. 1986).

*Primary Examiner*—Hezron E. Williams
*Assistant Examiner*—Louis M. Arana
*Attorney, Agent, or Firm*—Kirkland & Ellis

[57] ABSTRACT

There is provided a nondestructive inspection method and apparatus for determining fiber characteristics such as elasticity, diameter, and chemical composition, and the thickness and quality of fiber coatings via laser-generated ultrasound for velocity and attenuation measurements.

3 Claims, 4 Drawing Sheets

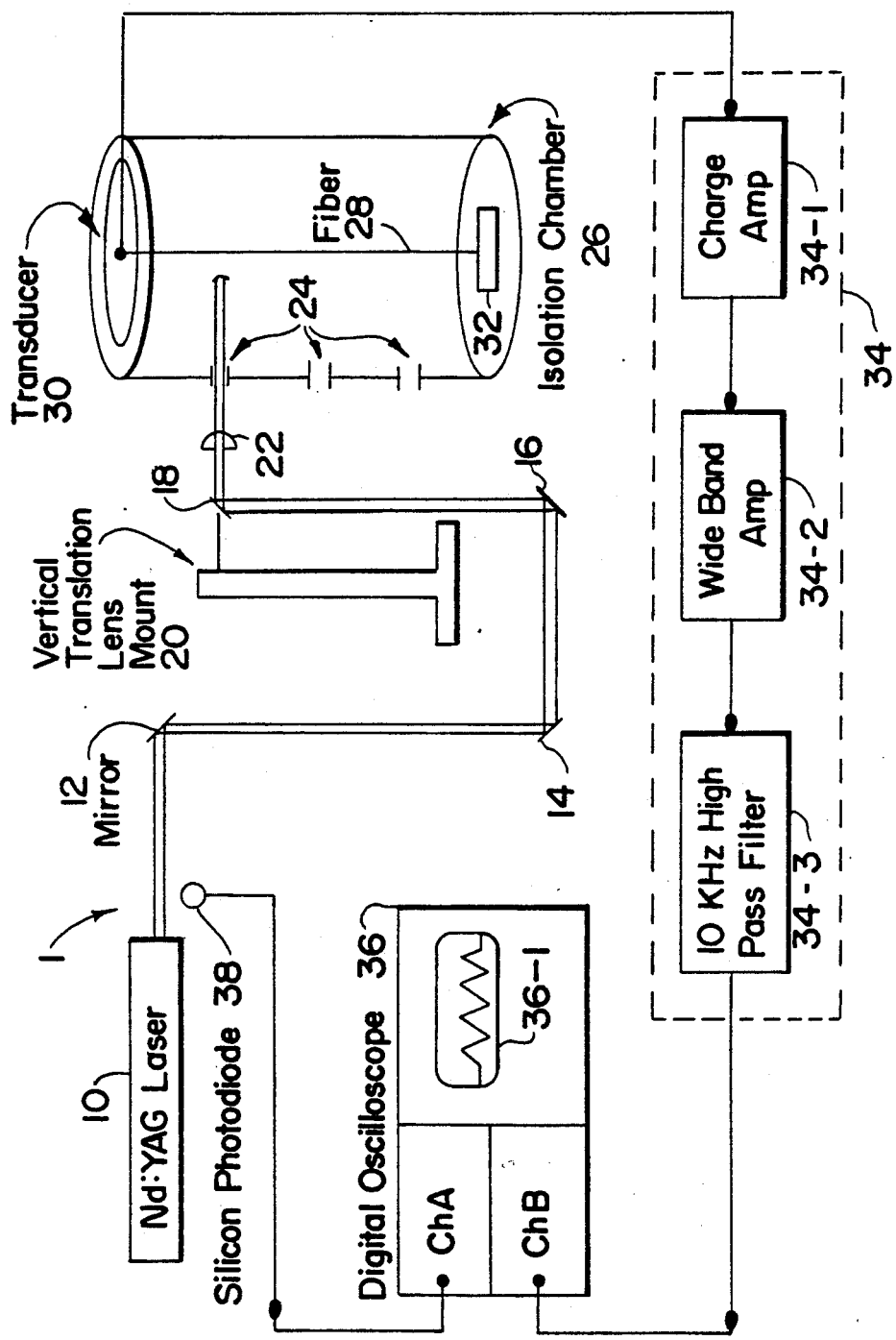
Fig—1

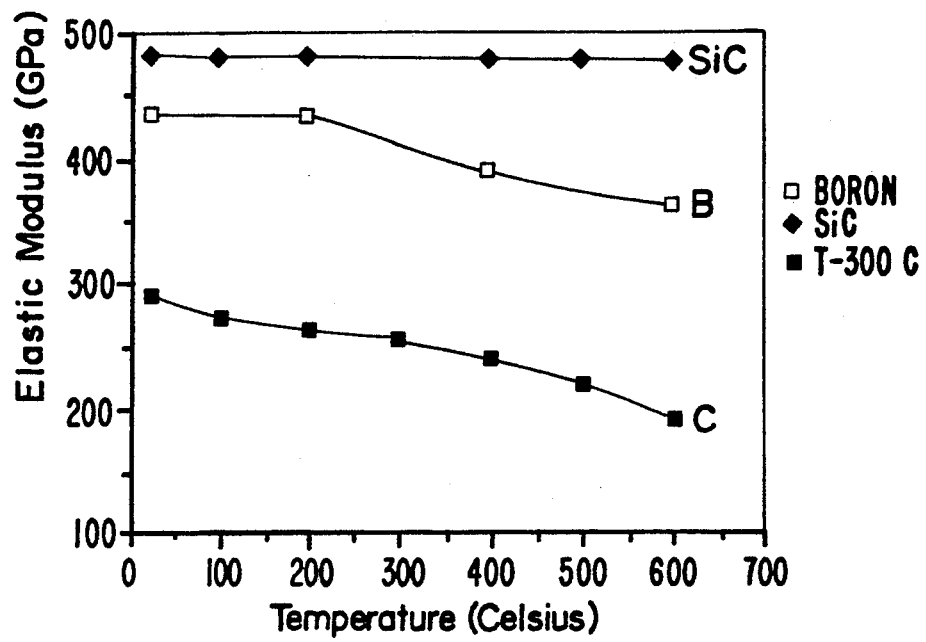
Fig_ 3
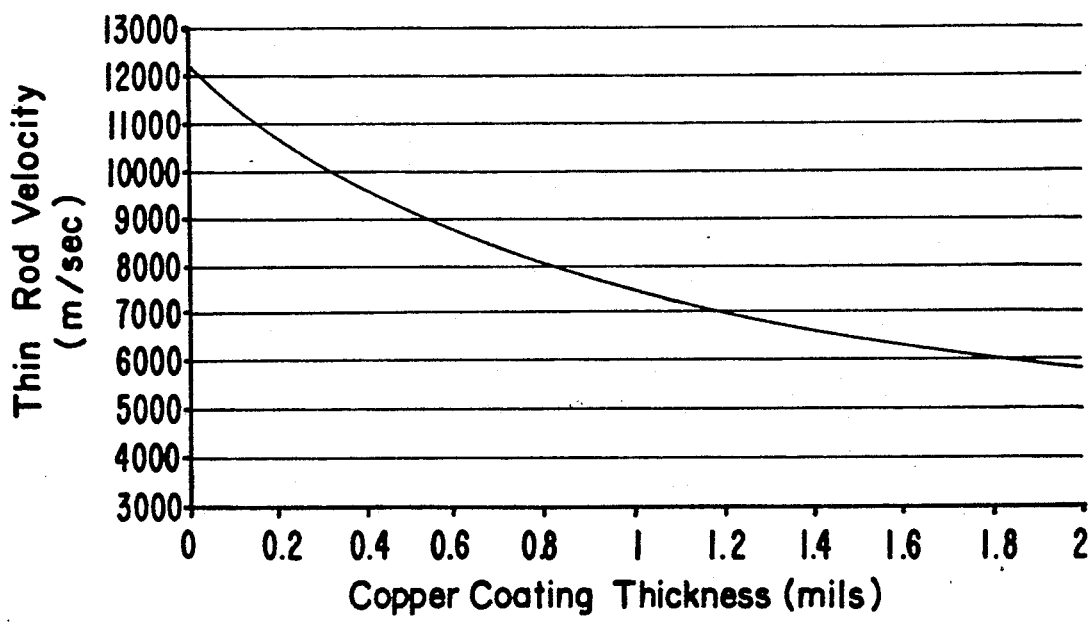
Fig_ 4

METHOD AND APPARATUS FOR LASER ULTRASONIC CHARACTERIZATION OF COATED FIBERS

The present invention relates to nondestructive testing of materials.

The use of fiber reinforcements in metallic and ceramic matrix materials has produced a new generation of engineering materials with exceptional specific stiffness and strength and superior high temperature performance. These properties are obtained through the interaction of the reinforcing fiber with the matrix material. Optimal properties are generally achieved only when the fiber is well bonded to the matrix materials. Unfortunately, many of the fibers and matrix materials are not chemically compatible; thus, coatings must be placed on the fibers to enhance their bond characteristics with the matrix materials and consistently achieve the desired mechanical and physical properties of the fiber-matrix interface. Coatings may also be used to enhance the characteristics of the fibers.

The coating thickness on the precursor fiber, the elastic properties of the coating, its structural integrity and its adherence to the fiber surface are of cardinal importance for the subsequent use of the fiber. The coating process must be carefully monitored and controlled to maintain the best combination of fiber and fiber-matrix interface properties. Measurement of the applied coating thickness and bonding is currently very difficult in an on-line environment, i.e., as the coated fiber is being produced.

A related problem is found in the communications industry with optical transmission fibers. These fibers are commonly made up of a silica (glass) core with a plastic (frequently nylon) coating. The coating is selected to enhance the flexibility, durability, and signal retention of the fiber. The fiber material should have an index of refraction substantially different from the core material to maintain the wave guide effectiveness of the fiber and thereby minimize transmission losses. The interface between the core and the coating is critical to both the flexibility and attenuation characteristics of the fiber. In some fibers the coating is designed to be bonded to the core; in others the coating should be completely unbonded. Disbonds in the bonded fibers or adhesions in the unbonded fibers can introduce high local loads on the core leading to fracture of the fiber or unacceptably high attenuation.

Prior methods and devices for testing fibers and coatings are not well suited to nondestructive, on-line evaluations of the thickness and bonding quality of coatings applied to fibers. For example, U.S. Pat. No. 4,710,030 to Tauc et al discloses an optical stress pulse generator and detection system for nondestructively measuring physical properties of sample films. A pump beam of short-duration electromagnetic pulses produces acoustic stress pulses in a sample while the change in the film's reflectivity induced by the stress pulses is detected by monitoring the intensity of a probe beam. Sound velocity and attenuation in the sample can be used to determine the thickness and bonding quality of the films.

U.S. Pat. Nos. 4,622,853 to Leugers and 4,674,332 to Pace et al disclose methods and devices that measure the propagation velocity of ultrasonic waves generated in moving webs by laser light pulses. The velocity measurements are used in real time to determine the strength parameters of the material, as well as its density and the orientation of physical domains within the material.

U.S. Pat. No. 4,754,645 to Piche et al discloses a method and apparatus for ultrasonically characterizing the polymer material held between axially aligned buffer rods. Piezoelectrically generated ultrasonic waves transmitted through one of the buffer rods interact with the polymer, and the phase and amplitude variations of the waves are continuously monitored through a transducer attached to the other buffer rod. Real time control of polymer processing conditions is thus provided.

U.S. Pat. No. 4,481,820 to Thomann discloses a method for determining the fineness and quantity of fibrous material by measurement of damping (attenuation) and propagation time delay of sound waves. These measured values may be used to control the production of fiber mixtures.

U.S. Pat. No. 4,493,217 to Engler et al discloses a process and apparatus for measuring travel time differences of ultrasonic pulses for measurements of gaseous flow fields. The propagation of a laser beam through the flow field is altered or modulated by ultrasonic pulses propagating through the flow.

Fiber properties cannot be conveniently measured using traditional ultrasonic techniques; thus, an alternative approach is needed to launch and detect appropriate ultrasonic waves in the fiber materials. Noncontact generation and detection of acoustic waves using pulsed laser generation and laser interferometric detection is disclosed in E. Bourkoff et al., "Noncontact Material Testing Using Low-Energy Optical Generation and Detection of Acoustic Pulses", Review of Progress in Quantitative Nondestructive Evaluation, vol. 5A, pp. 659–67, D. Thompson et al., eds., Plenum Press, New York (1986); D. Hutchins et al., "Phase Insensitive Detection of Laser-Generated Ultrasound," Appl. Phys. Lett., vol. 48, pp. 323–325 (Feb. 1986); C. Palmer et al., "Ultrasonic Nondestructive Materials Characterization of Rapidly Solidified Microstructures," Johns Hopkins Univ. Rpt. CMR-NDE-11 (Aug. 1983); and M. Rudd, "Ultrasonic Nondestructive Evaluation Using Laser Transducers," Review of Progress in Quantitative Nondestructive Evaluation, vol. 2B, pp. 1763–80, D. Thompson et al., eds., Plenum Press, New York (1983). Use of this approach to measure the velocity and attenuation of surface acoustic waves is disclosed in J. Burov et al., "High Accuracy Noncontact Laser-Optical Method for Measuring Surface Acoustic Wave Velocity and Attenuation," Appl. Phys. Lett., vol. 46, pp. 141–42 (Jan. 1985). Uses of this approach to measure the bulk elastic constants of composites and metallic glasses are disclosed in, respectively, L. Piche et al., "Laser Ultrasonics Measurement of Elastic Constants of Composites," Materials Evaluation, vol. 45, pp. 74–79 (Jan.-/Feb. 1987) and M. Rosen, "Ultrasonic Nondestructive Characterization of Metallurgical Reactions," Traitement du Signal, vol. 2, no. 1, pp. 243–52 (Spring 1985).

None of the patents or publications cited discloses the generation of ultrasound by laser pulses impinging on fibers nor the use of such ultrasound to characterize the internal structure of the fibers. For example, U.S. Pat. No. 4,710,030 is directed to measurements of films rather than fibers, and any acoustic waves generated are employed merely to change the surface reflectivity of the films rather than to determine the elastic properties of fibers and their coatings.

Recent advances in the generation and detection of ultrasonic waves in fibers offer a new approach to the characterization of the properties of coated fibers involving the generation and detection of ultrasonic waves in fibers to monitor elasticity, coating thickness, and adhesion. In this approach, a pulsed laser is used to excite an extensional ultrasonic wave in the fiber. This wave is detected at selected distances along the length of the fiber either by conventional or laser interferometric methods. The use of controlled multiple length rropagation paths permits absolute measurements of ultrasonic velocity and attenuation. These values can be related to the physical properties of the coated fiber to determine coating thickness and adhesion to the core.

The noncontact feature of both generation and detection of ultrasonic waves can be very advantageous in situations requiring physical separation between the measuring system and the material under investigation, for instance, when high temperatures or hostile atmospheres are involved. Furthermore, noncontact generation and detection precludes interaction with, and modification of, the wave propagation modes over a wide frequency range, thus enhancing the amount of information obtained from a single measurement.

SUMMARY

In accordance with the present invention, a method for nondestructively testing fibrous material comprises the steps of illuminating the fiber at a first position with a light pulse to generate vibrational waves in the fiber; detecting the vibrational waves at second position spaced a predetermined distance from the first position; and determining at least one of elasticity and thickness characteristics of the fiber.

In another aspect of the invention, an apparatus for nondestructively testing fibrous material comprises means for illuminating the fiber to generate vibrational waves in the fiber; means for detecting the vibrational waves; and means for determining at least one of an arrival time and an attenuation of the waves.

BRIEF DESCRIPTION OF THE DRAWINGS

The several objects and advantages of the present invention will be more apparent after a reading of the following detailed description in conjunction with the drawings in which:

FIG. 1 shows one embodiment of an apparatus for testing fibers in accordance with the present invention;

FIG. 2b shows details of the apparatus of FIG. 2a;

FIG. 3 shows relationships between fiber elastic modulus and temperature as measured by the apparatus of FIG. 1; and FIG. 4 shows a relationship between acoustic velocity and coating thickness.

DETAILED DESCRIPTION

Figure 2A:
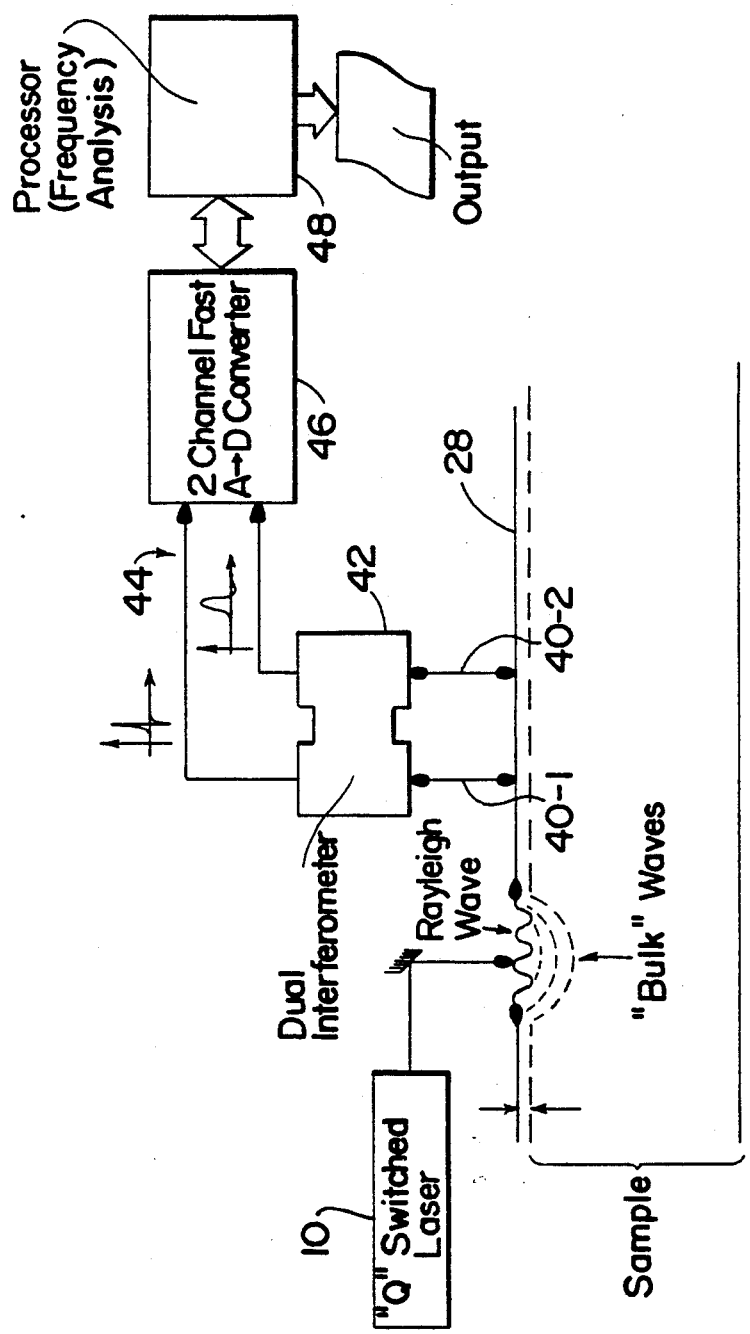
FIG. 2a shows another embodiment of an apparatus in accordance with the present invention.

In accordance with the present invention, compressive stress waves that propagate in a fiber under test are generated by transient loads applied by rapid energy transfer from an intense light source such as a single pulse from a Q-switched high energy Nd:YAG laser. Each laser pulse produces a thermoelastic stress pulse of short duration (15 ns) and relatively high amplitude (energy up to 200 millijoules in each laser pulse) making the investigation of very thin (e.g., 20 micrometers) fiber specimens of highly attenuating material possible.

It will be appreciated that other light sources such as nitrogen, ruby, dye, and carbon dioxide pulsed lasers may also be used.

The propagation of the stress wave through the material is determined by the elastic properties and attenuation (from absorption and scattering) of the material medium through which the stress wave moves. By examining the variations in the elastic properties and attenuation by means of sound wave velocity and amplitude measurements the quality and integrity of the material is assessed.

The stress waves may be detected by a piezoelectric transducer attached to the fiber as shown in FIG. 1. The laser beam can be moved to excite the stress waves at different known locations along the length of the fiber, providing calibration and correction of the data for ultrasonic velocity and attenuation by subtracting the response arrival time and amplitude at one travel distance from the similar information at a different distance. The change in arrival time as a function of the change in path length provides an accurate velocity measurement, and the change in amplitude as a function of the change in path length provides an accurate measure of the attenuation. From the sound wave velocity measurements the elastic properties of the composite (the fiber and its coating) are determined. The attenuation measurements provide a direct indication of the structural integrity of the coated fiber and extent of adhesion of the coating onto the fiber core because attenuation is increased by acoustic wave scattering from internal delaminations and flaws.

Referring to FIG. 1, there is shown an apparatus 1 in accordance with the present invention. An intense electromagnetic pulse is produced by a device 10 such as a neodymium-doped YAG laser. It will be appreciated that other types of pulsed energy sources, including pulsed lasers operating at other wavelengths, may also be used. The energy of each 15 nanosecond pulse produced by the Nd:YAG laser 10 is typically 200 millijoules.

Pulses from the laser 10 are conventionally directed by suitable means such as mirrors 12, 14, 16, and 18, one or more of which may be movably mounted on one or more suitable translation stages 20 (one is shown in FIG. 1). The laser pulses are also focussed by a concentrator 22, such as a suitable lens or mirror, that focussed the energy to the small area suitable for launching compressive stress waves. The concentrator 22 advantageously reduces the size of the laser spot on the material, e.g., the fiber surface, to a few micrometers, thereby causing highly localized generation of the sound waves. Increased energy density that can be achieved in this way is particularly important when examining highly attenuating fiber, and coated fiber materials. As described in more detail below, the translation stage 20 facilitates the direction of the laser pulses to different positions on the fiber under test.

It will be understood that the specific layout of the beam directing components and their type is determined mainly by the working space to maximize the convenience of carrying out the fiber measurements. A wide variety of mirrors, translation and rotation stages, and other components are commercially available from Newport Corp., Fountain Valley, Calif. and Melles Griot, Irvine, Calif. In addition, it will be appreciated that the diameter and focal length of the concentrator 22 is easily determined from well-known principles of geometrical optics.

In one embodiment, the light pulses are focussed by the concentrator 22 through a selected one of a plurality of ports 24 in an isolation chamber 26. The chamber 26 may advantageously provide special atmosphere and temperatures to a fiber under test 28. For determining strength-temperature relationships, the fiber 28 may be conventionally attached at one end to a suitable piezoelectric transducer 30, such as that manufactured by Panametrics, Inc. The other end of the fiber 28 is secured to means for stressing the fiber, such as a variable mass 32. The variable mass 32 allows the stress dependence of the elastic properties (derived from the ultrasonic wave velocity) to be determined.

It will be appreciated that the stress dependence of the elastic properties of composite fibers as functions of temperature is of great technological importance for many engineering applications. For example, as a result of nonlinearity of stress dependence and a negative thermal expansion coefficient, composites made from graphite fibers can exhibit important changes in properties with temperature. The Young's modulus for the direction along the reinforcing fibers in a composite can increase rather than decrease with temperature and the stresses generated can lead to yielding in the matrix and/or the fiber matrix interface. These effects can also lead to the sign and magnitude of the coefficient of thermal expansion being dependent on the temperature and thermal history of the composite. Both the dimensional and modulus changes could lead to instabilities in structures ranging from space stations to circuit boards.

It will be understood that the isolation chamber 26 may be a portion of a larger apparatus such as the equipment for drawing an optical communication fiber from a fiber preform.

The electrical signals produced by the piezoelectric transducer 30 are magnified and frequency shaped by a suitable electronic amplifier 34 that is conventionally selected according to considerations such as the impedance and sensitivity of the transducer 30. As illustrated in FIG. 1, the amplifier 34 may comprise a charge amplifier 34-1, a wideband amplifier 34-2, and a highpass filter 34-3. The wideband amplifier 34-2 typically need only provide gain for frequencies between 10 KHz and 2 MHz. The highpass filter 34-3 cuts off the lower frequency components of the transducer 30's output that are most heavily representative of noise and non-laser-generated vibrations of the fiber 28.

The electrical output of the amplifier 34 is connected to a suitable means for determining the amplitude and time of arrival of ultrasonic waves at the transducer 30, such as a digital oscilloscope 36. Also connected to the oscilloscope 36 is the output of a photodiode 38 which advantageously is used to trigger the operation of the oscilloscope 36 when the laser 10 emits a light pulse. The response of the transducer 30 as shaped by the amplifier 34 may be presented on the display 36-1 of the oscilloscope 36, which may be any suitable commercially available device, such as the EXPLORER-III digital oscilloscope manufactured by Nicolet Corp. and the DATA-6000 waveform analyzer manufactured by Analogic Corp. It will be understood that it is not necessary for the means for determining the amplitude and arrival time to display the transducer response; for example, a suitably triggered peak detector and timer can be used.

FIG. 2a illustrates an apparatus for carrying out the noncontact feature of both generation and detection of ultrasonic waves, which is very advantageous in situations requiring physical separation between the measuring system and the material under investigation, e.g., when high temperatures or hostile atmospheres are involved. Furthermore, the contactless generation and detection precludes interaction with, and modification of, the sound wave propagation pattern under study.

Propagation of ultrasonic waves in a medium causes surface displacements on the material that are measured optically by exploiting the phase shift of an optical beam reflected from the surface of the material. When the reflected beam is combined with a reference optical beam from a helium-neon laser, optical phase changes are converted into amplitude changes that are detectable by a sensitive photodiode. These variations in amplitude are proportional to the surface displacements on the specimen. As shown in FIG. 2a, two optical probes 40-1, 40-2 are separated to allow accurate measurements of travel time of an ultrasonic wave in the material over a well-defined distance. Furthermore, the variation in magnitude of the surface displacements detected by the two interferometers determines the ultrasonic attenuation in the material. Thus, both velocity and attenuation can be measured simultaneously.

The two optical probes are advantageously generated by a dual probe laser interferometer 42 which includes a pair of Fizeau interferometers. The outputs 44 of the interferometer 42 may be separately digitized by a suitable analog-to-digital converter 46 and further processed by any suitable spectrum analyzer 48 such as the Analogic Corp. instrument mentioned above. Nevertheless, it will be appreciated that sound velocity and attenuation data can be derived directly from the analog outputs 44 of the dual interferometer 42 by directly comparing those outputs on an oscilloscope or other suitable instrumentation such as that shown in FIG. 1.

Figure 2B:
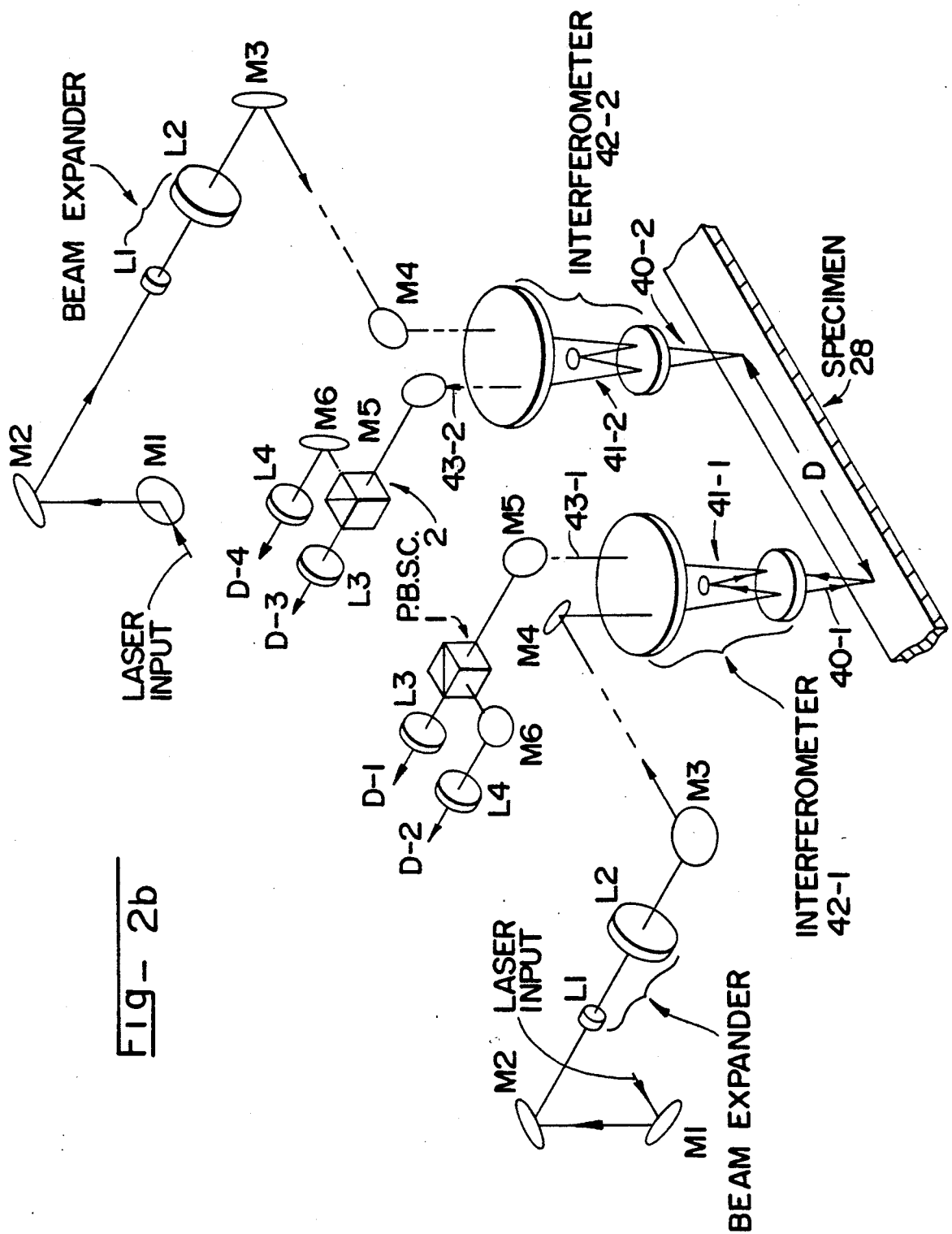

Referring to FIG. 2b there is shown a detailed view of the dual laser interferometer 42. Light from suitable lasers such as helium-neon gas lasers is expanded, collimated, and directed by conventional components M1–M4, L1, L2 to each of a pair of Fizeau-type interferometers 42-1, 42-2. Probe beams 40-1 and 40-2 exit and are reflected to the interferometers as shown, wherein they are combined with reference beams 41-1 and 41-2 as described above. The amplitudes of the combined beams 43-1 and 43-2, and thus the surface displacement of the specimen or fiber 28, are then detected by suitable photodiodes D1–D4 which produce outputs 44. The position sensitivity of the dual laser interferometer 42 can be increased by including polarizing beamsplitter cubes P.B.S.C.-1 and P.B.S.C.-2 and subtracting the orthogonally polarized pairs of detector outputs D1–D2, and D3–D4. It will be appreciated that other types of interferometer, such as those discussed in the above-cited publications, may also be used.

The technique of determining ultrasonic wave velocity by measuring arrival time and attenuation has been applied to different types of uncoated fibers at different temperatures. The velocities were then used to calculate the strengths of the fibers according to well-known relationships between velocity, density and elastic modulus that are set forth in, for example, E. Schreiber et al., "Elastic Constants and Their Measurement," McGraw-Hill, New York (1973) and the above-cited publication by L. Piche et al. For example, Young's modulus E can be calculated from:

$$VEL^2_e = \rho E$$

where $\rho$ is the density and $VEL^2_e$ is the extensional wave velocity which is measured directly. The extensional velocity is measured in thin fibers and rods, i.e., where the diameter of the fiber is much less than the wavelength of the acoustic wave.

Using the relationships described above, the apparatus 1 has been used to determine the elastic moduli of boron, silicon carbide, and graphite fibers that are typically used in reinforced composites. Results of the calculations based on velocity measurements at the several points indicated are shown in FIG. 3. The uppermost curve indicates a nearly constant elastic modulus for silicon carbide fibers at temperatures from 25°–600° C. The middle curve shows a decreasing elastic modulus for boron fibers at temperatures from 200°–600° C. The lowest curve indicates a decreasing elastic modulus for graphite fibers at temperatures from 25°–600° C. It has been found that fibers typically exhibit nonlinear elasticity with the amount and character of the nonlinearity, i.e., the change in modulus and curvature of the modulus-temperature curve, being influenced by the manufacturing conditions of and orientations of crystallites in the fibers. It will also be appreciated that the apparatus and method can also be used to determine the strength of the glassy fibers used for optical communications.

The present invention also enables the determination of important characteristics of coated fibers. For example, the thickness of the fiber core's coating can be derived from the measured acoustic wave velocity in the coated fiber as follows.

As described above, the velocity of an acoustic wave in a thin rod is a function of the rod's elastic modulus and density. Since these parameters follow the rule of mixtures for composite materials, the acoustic velocity also follows the rule of mixtures. Accordingly, the acoustic velocity of a coated fiber is given by:

$$VEL_{coated\,fiber} = (VEL_{core})(vol_{core}) + (VEL_{coat})(vol_{coat})$$

where V denotes the extensional wave velocity in the subscripted material and v denotes the volume fraction of the subscripted material. Since the volume fraction must sum to unity, it is easy to see that:

$$vol_{core} = \frac{VEL_{coated\,fiber} - VEL_{coat}}{VEL_{core} - VEL_{coat}}$$

Recognizing that the average thickness of the coating is one-half the difference of the diameters of the core and the coated fiber, the thickness $t_{coat}$ of the coating is given by:

$$t_{coat} = \tfrac{1}{2}\{d - [(vol_{core})(d^2)]^{\frac{1}{2}}\}$$

where d is the diameter of the coated fiber.

The expected relationship between measured sound wave velocity and coating thickness for copper-coated, 100-micrometer-diameter silicon carbide fibers is shown in FIG. 4. With the apparatus 1 described above, it is possible to measure the acoustic velocity with an accuracy of approximately 1%. Accordingly, coating thickness changes of less than 250 nanometers for thin coatings and of less than 1.3 micrometers for thicker coatings can be identified.

It will be appreciated by those of ordinary skill in the art that both apparatuses described above are independent of the wavelength of the acoustic waves in the fibers because the extensional velocity measurements are carried out in the non-dispersive regime. In addition, changes between the values of extensional wave velocity measured at several points along a fiber under test indicate variations in fiber composition, thickness, etc. between the measurement points.

The present description and drawings are intended in all senses to be illustrative rather than restrictive and those variations and modifications that become apparent to those of ordinary skill in the art but are contained within the spirit and scope of the invention, which is to be delimited solely by the appended claims, are intended to be included therein.

What is claimed is:

1. A method of nondestructively measuring the thickness of a coating on a fiber comprising the steps of:
    applying longitudinal stress to the fiber;
    illuminating the fiber at a first position with a light pulse to generate vibrational waves in the fiber;
    detecting the vibrational waves at a second position spaced a predetermined distance from the first position; and
    determining the thickness of the coating on the fiber according to the equations:

$$vol_{core} = \frac{VEL_{coated\,fiber} - VEL_{coat}}{VEL_{core} - VEL_{coat}}$$

and $$t_{coat} = \tfrac{1}{2}\{d - [(vol_{core})(d^2)]^{\frac{1}{2}}\};$$

wherein $t_{coat}$ is the thickness of the coating on the fiber, d is the diameter of the coated fiber, $vol_{core}$ is the volume fraction of the core fiber, $VEL_{coated\,fiber}$ is the extensional wave velocity of the vibrational waves in the coated fiber, $VEL_{coat}$ is the extensional wave velocity of the vibrational waves in the coating, and $VEL_{core}$ is the extensional velocity of the vibrational waves in the core fiber.

2. The method of nondestructively measuring the thickness of a coating on a fiber of claim 1, wherein a piezoelectric transducer is used to detect the vibrational waves.

3. The method of nondestructively measuring the thickness of a coating on a fiber of claim 1, wherein an interferometer is used to detect the vibrational waves.

* * * * *